(12) United States Patent
Shah et al.

(10) Patent No.: US 7,896,806 B2
(45) Date of Patent: Mar. 1, 2011

(54) SPECULUM COVER

(75) Inventors: Tilak M. Shah, Cary, NC (US); Dezso K. Levius, Cary, NC (US)

(73) Assignee: Polyzen, Inc., Apex, NC (US)

( * ) Notice: Subject to any disclaimer, the term of this patent is extended or adjusted under 35 U.S.C. 154(b) by 588 days.

(21) Appl. No.: 11/940,103

(22) Filed: Nov. 14, 2007

(65) Prior Publication Data

US 2008/0114210 A1    May 15, 2008

Related U.S. Application Data

(60) Provisional application No. 60/865,958, filed on Nov. 15, 2006.

(51) Int. Cl.
*A61B 1/32* (2006.01)
(52) U.S. Cl. .................. 600/203; 600/186; 600/206; 600/220
(58) Field of Classification Search .............. 264/80; 600/184–246
See application file for complete search history.

(56) References Cited

U.S. PATENT DOCUMENTS

| 5,644,798 | A |   | 7/1997 | Shah |
| 5,679,423 | A |   | 10/1997 | Shah |
| 6,152,596 | A | * | 11/2000 | Fraden ................. 374/158 |
| 6,432,048 | B1 | * | 8/2002 | Francois ............... 600/220 |
| 6,902,530 | B1 |   | 6/2005 | Pianka |

* cited by examiner

*Primary Examiner*—Eduardo C Robert
*Assistant Examiner*—Christina Negrelli
(74) *Attorney, Agent, or Firm*—Richard T. Matthews; Steven J. Hultquist; Hultquist IP

(57) ABSTRACT

A speculum cover that is adapted to sheath the blades of a speculum, and to support lateral vaginal walls to facilitate vaginal/cervical examination during gynecological exams and surgery. The speculum cover includes top and bottom pockets for the respective blades of the speculum, and side portions having openings therein for sampling of tissue at the vaginal locus. In a specific implementation, the speculum cover is of a four-ply construction, formed by impulse welding or other polymeric film joining technique, and the two inner plies of the cover include rearwardly extending flaps to which are adhesively secured donning guide members for facilitating installation of the cover on the speculum.

19 Claims, 2 Drawing Sheets

SPECULUM COVER

FIELD OF THE INVENTION

The present invention relates to a vaginal speculum cover that is adapted to support lateral vaginal walls to facilitate vaginal/surgical examination during gynecological exams and vaginal/cervical surgery.

DESCRIPTION OF THE RELATED ART

In conventional gynecological practice, gynecological examinations are conducted with a vaginal speculum, which is adapted to lift upper and lower vaginal walls to facilitate the requisite examination. In many instances, however, lateral vaginal walls are at least partially collapsed and obstruct view of the vaginal locus.

As a result of such tissue collapse, the gynecological examinations are rendered more difficult.

U.S. Pat. Nos. 6,432,048 and 6,902,530 address this problem and present designs for membrane structures serving to prevent such lateral vaginal wall collapse, but such solutions have not been adopted commercially, due to problems of manufacturability and ease and simplicity of use.

There is accordingly a compelling need in the art for an improved vaginal speculum cover to facilitate unobstructed viewing of the vaginal/cervical locus even when lateral wall collapse is present in a patient.

SUMMARY OF THE INVENTION

The present invention relates to a vaginal speculum cover that is adapted to support lateral vaginal walls to facilitate vaginal/surgical examination during gynecological exams and vaginal/cervical surgery.

In one aspect, the invention relates to a speculum cover comprising a main body portion including a top pocket and a bottom pocket, each extending from a proximal end portion of the main body portion to a distal end portion thereof, with each said top and bottom pockets being bounded by welded seams, with each pocket at its distal portion being bounded by a distal end seam, with the cover having side portions each including a marginal seam immediate the top and bottom portions of the cover, with at least one opening in each side portion of the cover, said cover comprising a polymeric film material of construction.

In another aspect, the invention relates to method of making a speculum cover, comprising:
  providing four superposed sheets of thermoplastic material;
  welding the four superposed sheets along an outer edge to form an outer edge seam;
  separating the innermost facing sheets from one another, and longitudinally welding the two top sheets to one another along lateral portions of the two top sheets and longitudinally along lateral portions of the bottom two sheets, to form a top pocket between the top two sheets and a bottom pocket between the bottom two sheets; and
  welding the top two sheets at a distal portion thereof and welding said bottom two sheets at a distal portion thereof, whereby the pocket formed between the top two sheets is closed at its distal portion and the pocket formed by the bottom two sheets is closed at its distal portion.

In a further aspect, the invention relates to a method of donning a speculum cover on a speculum, comprising providing a sheath as described above, having donning guides affixed to each of the top and bottom pockets, said method comprising:
  inserting upper and lower blades of a speculum into said top and bottom pockets of the cover, utilizing the donning guides to guide insertion, and reposing the upper and lower blades of the speculum in the top and bottom pockets, respectively, of the speculum; and
  removing the donning guides from the speculum cover.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The present invention relates to a vaginal speculum cover that prevents vaginal wall collapse that otherwise would obstruct a physician's visibility during vaginal/cervical surgery or gynecological examination.

As described more fully hereinafter, the vaginal speculum cover of the present invention is secured on the blades of the speculum and adapted to permit free movement of the speculum blades between a closed position during insertion into the vaginal locus, and an open position in which the speculum dilates the vagina for visualization of the vaginal locus and/or cervix.

The speculum cover of the present invention may be formed of any suitable polymeric material, or alternatively of other suitable material of construction. Polymeric thermoplastic materials are preferred, most preferably thermoplastic elastomeric polymers. Polymeric thermoplastic materials that can be utilized in the broad practice of the present invention in specific embodiments thereof, include, without limitation, thermoplastic olefins, styrenic block copolymers, thermoplastic polyurethane elastomers, copolyesters, copolyamides, and various blends and copolymers of monomers of the foregoing materials. In preferred practice, the speculum cover is fabricated from polyurethane elastomer film. Such film may for example have a thickness on the order of 1.2-1.5 mils, although any suitable thickness appropriate to the particular application may be employed. A preferred polyurethane film material is polyurethane TSP 1065, commercially available from Polyzen, Inc. (Apex, N.C.).

The speculum cover includes sleeve pockets for the respective blades of the speculum. The speculum cover in one embodiment is provided with handles that can be secured to the cover by a low tack adhesive to permit ready removal of the handles from the cover after installation of the speculum cover on the speculum. The speculum cover in various embodiments has a tapered conformation to assist in opening of the speculum to a full width (with full extension of the blades of the speculum) in use. The speculum cover of the invention in another embodiment features at least one fenestrated opening enabling collection of tissue samples to be readily conducted.

The polymeric film employed as a material of construction for the speculum cover advantageously has a modulus that permits the cover to support and withstand lateral wall pressure in the vaginal locus so as to prevent lateral wall collapse that would otherwise obstruct the view of the physician conducting gynecological visual examination or performing vaginal/cervical surgery.

Figure 1:
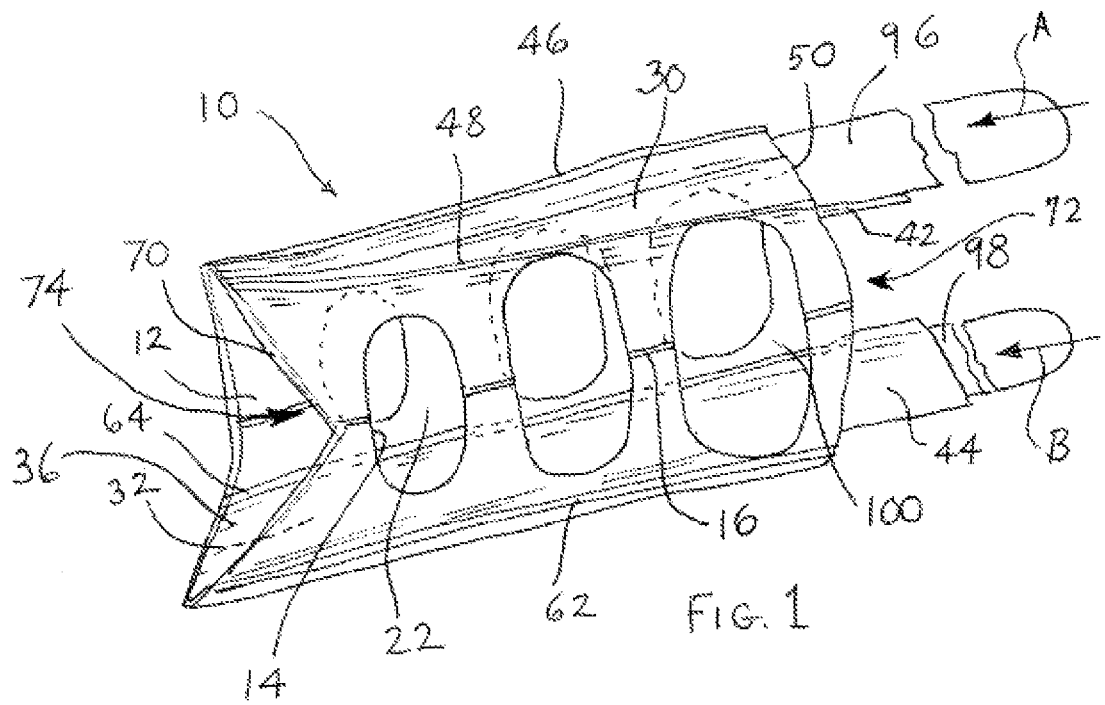
FIG. 1 is a perspective view of the speculum cover of the present invention, according to one embodiment thereof.

Referring now to the drawings, FIG. 1 is a perspective view of a speculum cover 10, according to one embodiment of the invention.

The speculum cover 10 includes a main body portion 12, defining a proximal opening 72 and a distal opening 74. The speculum cover is shown in a lay-flat conformation in FIG. 2, and as installed on a speculum in FIG. 3, with the reference numerals of corresponding parts and features in FIGS. 2 and 3 being the same as those used in FIG. 1.

Figure 3:
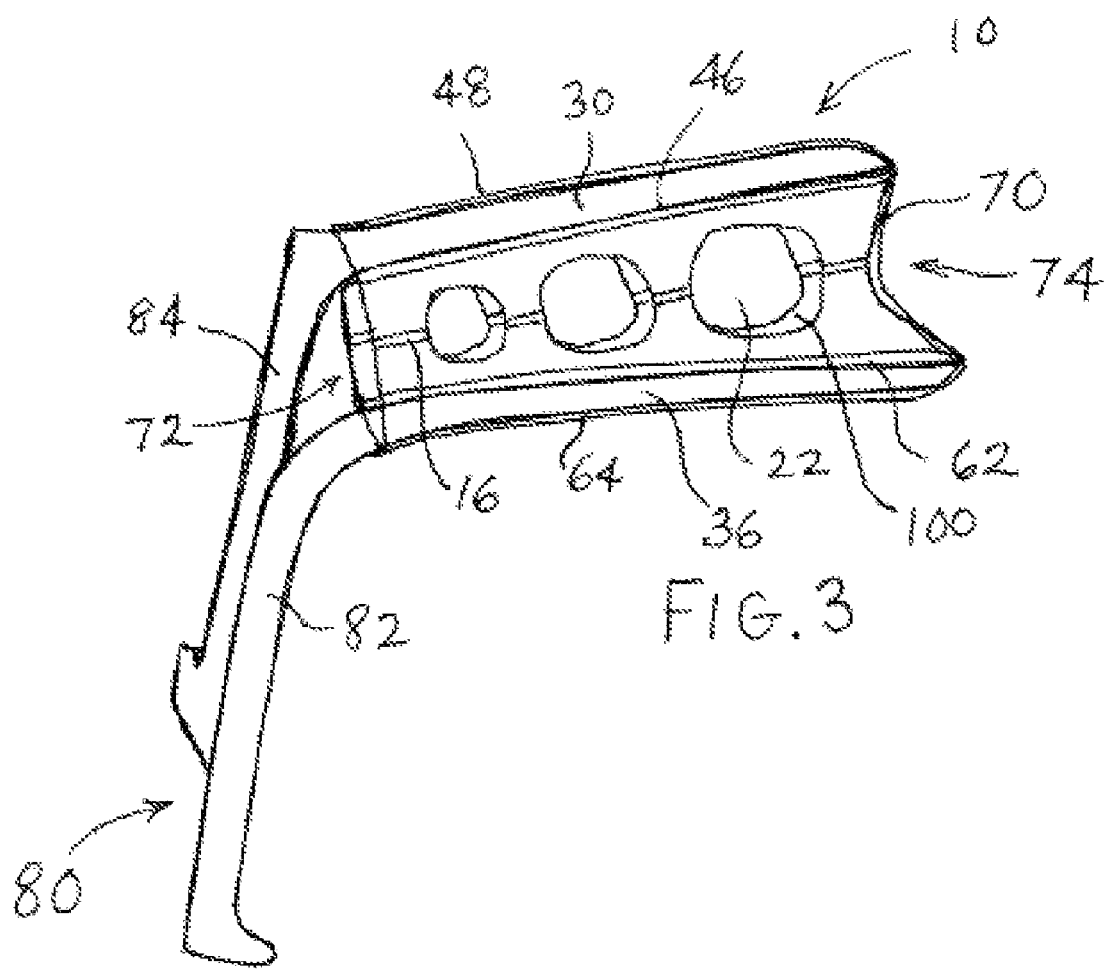
FIG. 3 is a perspective view of the speculum cover of the invention, as installed on a speculum, according to one embodiment of the invention.

The speculum cover 10 is formed of superposed sheets that are film welded, at the top and bottom portions of the cover, to form respective pockets accommodating insertion of the blades of the speculum, as illustrated in FIG. 3.

The pockets include an upper pocket 30 defined by two layers of film material bonded at top pocket right seam 46 and top pocket left seam 48, to enclose a top pocket interior volume 50 therebetween, in which such interior volume of the pocket extends from the proximal end to the distal end of the cover.

In like manner, the superposed film layers at the bottom portion of the cover are film welded at bottom pocket left seam 62 and bottom pocket right seam 64 to form a bottom pocket providing a bottom pocket interior volume 32, for insertion thereinto of a lower blade of a speculum, as shown in FIG. 3.

The top pocket and bottom pocket therefore are coextensive in length with the main body portion 12 of the cover and the superposed films at the top portion of the cover are welded to one another by a distal end seam 70, as are the superposed films at the bottom portion of the cover.

Figure 2:
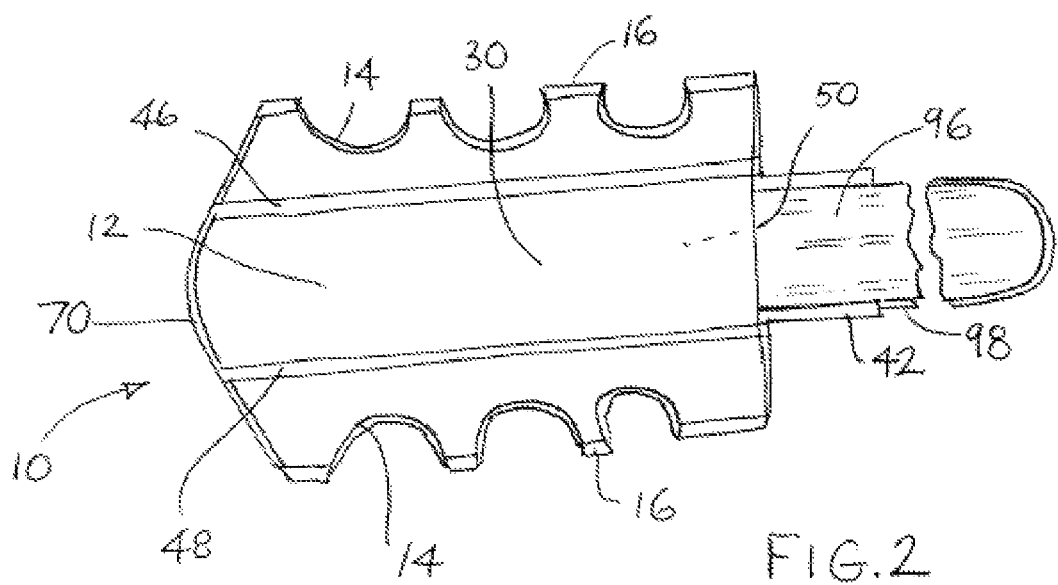
FIG. 2 is a top plan view of the speculum cover of FIG. 1, in a lay-flat conformation.

Referring to FIG. 2, the superposed sheets forming the top portion of the cover are welded to one another at the top pocket right seam 46 and the top pocket left seam 48, outside of which the superposed sheets extend laterally outwardly to marginal extremities at which the superposed sheets are welded to one another by marginal seams 16. The marginal portions of the cover exhibit cut-outs 14, which when the cover is installed as shown in FIG. 3, or vertically extended as shown in FIG. 1, form side openings 22 permitting access to vaginal walls for tissue collection, examination, etc. Such openings may increase in size from the distal end to the proximal end or alternatively may increase in size from the proximal end to the distal end, as may be desired in a given embodiment of the invention.

Thus, as is apparent from the foregoing, the sheath may be manufactured by superposing four layers or plies of the thermoplastic film material, followed by welding to form the respective marginal seams 16, and the cut-outs 14 may be formed concurrently with or subsequent to such film welding. For example, the cut-outs 14 may be formed by die cutting of the superposed sheets.

Subsequent to edge welding of the sheets, the top and bottom pocket seams 46, 48, 62 and 64 may be formed, with insertion into the inner two sheets of the four-ply assembly of a parting element of appropriate character, to permit welding of the seams 46, 48, 62 and 64, such as by impulse welding.

In general, the seams of the cover may be formed in any suitable manner and using any suitable film bonding or joining techniques, including, without limitation, impulse welding, radio frequency (RF) welding, solvent welding, adhesive bonding, or other suitable film joining techniques. In general, the seams must be physically robust, to accommodate insertion of the speculum blades into the top and bottom pockets of the cover, and to accommodate stretching of the cover with pressure on the seams, without breakage or other failure of the cover in use. Impulse welding is presently preferred to form the respective seams of the cover.

It will be recognized that the foregoing four-ply construction affords a ready technique that is well-adapted for mass production of the cover articles of the invention. Nonetheless, it is also contemplated that the cover at its side portions containing side openings 22 may be of single-ply character rather than double-ply as above described. The four-ply technique, however, affords manufacturing advantages and is preferred in use.

As shown in FIGS. 1 and 2, the inner plies at the top and bottom of the cover include rearwardly extending flaps, including top pocket proximal flap 42 and bottom pocket proximal flap 44 (the bottom flap 44 is not shown in FIG. 42, since it is covered by top pocket proximal flap 42). These flaps in one embodiment of the invention may be coated on a portion of the exposed interior facing surfaces thereof, posterior to the main body portion 12 of the cover, with a low tack adhesive material. Such low tack adhesive material serves to secure such flaps to the respective donning guides 96 and 98.

The donning guides may be formed of any suitable material of construction, such as cardboard, wood, plastic, etc. In one embodiment, such guides are formed of Mylar® material, of an appropriate thickness for the stiffness necessary for the guide function.

The top pocket donning guide 96 therefore extends into the top pocket 30, being reposed in the top pocket interior volume 50. In like manner, the bottom pocket donning guide 98 is affixed to the bottom pocket proximal flap, with the donning guide 98 extending into the bottom pocket 36 and reposed in the interior volume 32 thereof.

By this arrangement of donning guides secured to the inner plies forming the pocket, the cover is adapted for ready installation on a speculum, with the upper blade of the speculum being guided by the donning guide 96 in the direction indicated by arrow A and the bottom blade of the speculum being guided by donning guide 98 into the pocket in the direction indicated by arrow B. The donning guides therefore permit the donning of the cover on the sheath to be readily manually effected without undue effort.

Subsequent to insertion of the speculum blades into the respective top and bottom pockets of the cover, the donning guides 96 and 98 may simply be pulled rearwardly (in the proximal direction) to disengage them from the associated inner ply flaps 42 and 44. The flaps then may remain free, or if they have residual low tack adhesive material thereon, they may be secured to the associated blade surface of the speculum.

Alternatively, the flaps may be provided with low-tack adhesive on both sides thereof, whereby the flap can be folded back into the interior cavity 100 of the cover, to be retained in a "folded back" position during subsequent use of the speculum.

FIG. 3 shows the cover 10 as installed on a speculum, with the speculum blades being fully extended. The speculum 80 includes a speculum lower blade/handle member 82 and a speculum upper blade/handle 84. The respective blade/handle members are hingedly secured to one another, so as to be pivotally manipulable by a gynecologist, to extend the top blade upwardly in relation to the lower blade, so that the cover assumes the conformation shown in FIG. 3.

In use in such conformation, the side openings 22 of the cover allow access to the vaginal walls at either side of the sheath, as well as provide unobstructed viewing of the vaginal/cervical locus.

It will therefore be appreciated that the cover of the present invention is readily fabricated and affords a substantial advance of the art, relative to manufacturability and mass production of sheath and cover articles of the prior art.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

The invention claimed is:

1. A welded multiple sheet speculum cover comprising a welded multiple sheet main body portion including a top pocket and a bottom pocket, each extending from a proximal end portion of the main body portion to a distal end portion thereof, with each said top and bottom pockets being bounded by longitudinally extending welded seams, with each pocket at its distal portion being bounded by a distal end welded seam, with the cover having side portions each including a longitudinally extending marginal welded seam intermediate the top and bottom portions of the cover, with at least one opening in each side portion of the cover, said cover comprising a polymeric film material of construction.

2. The speculum cover of claim 1, wherein the cover is of four-ply construction.

3. The speculum cover of claim 1, wherein each side portion of the cover includes multiple side openings.

4. The speculum cover of claim 1, wherein the top and bottom pockets of the cover are each bounded by upper and lower layers of film material, and the inner layers bounding the pocket include a rearwardly extending flap.

5. The speculum cover of claim 4, further comprising donning guides secured to said flaps.

6. The speculum cover of claim 1, wherein side portions of the cover include openings that increase in size in a lengthwise direction of the side portion of the cover.

7. The speculum cover of claim 6, wherein said lengthwise direction is from distal end portion toward the proximal end portion of the cover.

8. The speculum cover of claim 6, wherein the lengthwise direction is from the proximal end portion toward the distal end protion of the cover.

9. The speculum cover of claim 1, formed of a thermoplastic elastic polymer selected from the group consisting of: thermoplastic olefins; styrenic block copolymers; thermoplastic polyurethane elastomers; copolyesters; copolyamides; and blends and copolymers of monomers of the foregoing materials.

10. The speculum cover of claim 1, wherein the cover comprises a thermoplastic polymeric urethane material of construction.

11. The speculum cover of claim 1, wherein inner sheets of the top and bottom pockets extend rearwardly beyond the proximal end portion of the main body portion to form rearwardly extending flaps, and donning guides are adhesively secured to the rearwardly extending flaps.

12. A method of making a welded multiple sheet speculum cover, comprising:
   providing four superposed sheets of thermoplastic material;
   longitudinally welding the four superposed sheets along an outer edge to form a longitudinally extending outer edge weld seam;
   separating the innermost facing sheets from one another, and longitudinally welding the two top sheets to one another along lateral portions of the two top sheets and longitudinally along lateral portions of the bottom two sheets, to form a top pocket between the top two sheets and a bottom pocket between the bottom two sheets; and
   welding the top two sheets at a distal portion thereof and welding said bottom two sheets at a distal portion thereof, whereby the top pocket formed between the top two sheets is closed at its distal portion and the bottom pocket formed by the bottom two sheets is closed at its distal portion, and wherein when the speculum cover is extended to an open position, the sheets connecting the top pocket and the bottom pocket to one another form side walls of the speculum cover, each side wall having the longitudinally extending outer edge weld seam extending longitudinally along it, intermediate the top and bottom portions of the speculum cover.

13. The method of claim 12, further comprising cutting an arcuate cutout at the side portions of the superposed four sheets, said arcuate cutout forming a side opening when the speculum cover is installed on a speculum.

14. The method of claim 12, wherein the four sheets are formed of a material selected from the group consisting of: thermoplastic olefins; styrenic block copolymers; thermoplastic polyurethane elastomers; copolyesters; copolyamides; and blends and copolymers of monomers of the foregoing materials.

15. The method of claim 12, wherein the four superposed sheets are formed of thermoplastic polyurethane material.

16. The method of claim 12, further comprising forming a rearwardly extending flap on each of the two interior sheets of the four superposed sheets.

17. The method of claim 16, further comprising affixing to each of said flaps a donning guide.

18. The method of claim 12, wherein said welding comprises impulse welding.

19. A method of donning a speculum cover on a speculum, comprising providing a sheath as claimed in claim 1, having donning guides affixed to each of the top and bottom pockets, said method comprising:
   inserting upper and lower blades of a speculum into said top and bottom pockets of the cover, utilizing the donning guides to guide insertion, and reposing the upper and lower blades of the speculum in the top and bottom pockets, respectively, of the speculum; and
   removing the donning guides from the speculum cover.

* * * * *